United States Patent [19]
Makino et al.

[11] Patent Number: 5,899,665
[45] Date of Patent: May 4, 1999

[54] METHOD AND APPARATUS FOR CONTROLLING INFUSION VOLUME

[75] Inventors: Hideo Makino; Kenji Katayama; Yoshitaka Takeda, all of Akaiwa-gun, Japan

[73] Assignee: ALARIS Medical Systems, Inc., San Diego, Calif.

[21] Appl. No.: 08/872,843

[22] Filed: Jun. 11, 1997

[51] Int. Cl.[6] .................................................. F04B 49/00
[52] U.S. Cl. ............................... 417/20; 417/18; 604/67; 604/253
[58] Field of Search .................................. 417/43, 20, 18, 417/63; 604/50, 67, 253

[56] References Cited

U.S. PATENT DOCUMENTS

| | | | |
|---|---|---|---|
| 4,786,800 | 11/1988 | Kamen | 250/222.1 |
| 4,857,048 | 8/1989 | Simons et al. | 604/50 |

Primary Examiner—Timothy S. Thorpe
Assistant Examiner—Paol L. Ratcliffe
Attorney, Agent, or Firm—Fulwider Patton Lee & Utecht, LLP

[57] ABSTRACT

A flow sensor detects drops of infusion fluid that enter the drip chamber of an infusion system and generates a drop-detection signal indicating each drop detected. A setting controller receives the drop-detection signals from the flow sensor and counts the drops detected and then determines the fluid-flow rate of infusion fluid into the drip chamber. The setting controller then sets the infusion pump so that the fluid-flow rate of the infusion pump substantially matches the fluid-flow rate of the drip chamber. A motion sensor detects drip-chamber movement and generates a motion-detection signal indicating the motion state of the drip chamber. A maintaining controller is coupled to receive the motion-detection signal from the motion sensor. The maintaining controller also stores a signal that indicates a stationary drip chamber. The maintaining controller compares the motion-detection signal to the stored signal to determine if drip chamber movement has occurred, and if drip-chamber movement has occurred it maintains the fluid-flow rate of the infusion pump as set immediately prior to the detection of drip-chamber movement.

18 Claims, 4 Drawing Sheets

METHOD AND APPARATUS FOR CONTROLLING INFUSION VOLUME

BACKGROUND OF THE INVENTION

The invention relates generally to infusion systems, and more particularly, to an apparatus and method for controlling the volume flow rate of infusion fluid through an infusion pump.

A typical infusion system for use in the medical field includes an infusion fluid container that supplies infusion fluid to a drip chamber. The drip chamber is typically made of a transparent resin. The drip chamber, in turn, supplies the fluid to an infusion tube which passes through an infusion pump. As disclosed in Japanese patent publication No. Hei-4-51963, an apparatus and method for controlling infusion volume typically involves setting the rate at which fluid flows through the infusion pump to match the rate at which fluid flows into the drip chamber. A photo coupler flow sensor is used to detect drops of fluid entering the drip chamber. The number of drops of fluid dripping into the drip chamber is counted over a specified period of time by a computer, typically contained in the infusion pump. The volume flow rate of fluid into the drip chamber is then calculated by the computer. Using this calculated volume flow rate, the infusion-pump motor is adjusted so that the desired volume flow rate of fluid through the infusion pump matches the measured flow rate into the drip chamber.

Under a steady-state environment, i.e., one in which the drip chamber remains motionless, the method and apparatus of controlling volume flow rate as just described provides smooth and continuous infusion. However, in some environments in which infusion systems operate, it is generally impracticable to expect a drip-chamber to remain motionless. A sway or vibration of the drip chamber may occur at a bedside or in a clinical environment due to the movement of a patient. Uncontrollable environmental conditions, such as wind, may also cause the drip chamber to move.

When the drip chamber experiences such movement, existing sensors may not successfully accommodate for the effect such movement has on the operation of the drip chamber. This is because the accuracy of the flow rate is largely dependent on the accuracy of the drip-chamber drop count. If the drip chamber is caused to sway or vibrate, the flow sensor may not detect all the drops and accordingly the count is inaccurate. If movement occurs and the drip-chamber drop count is inaccurate, the infusion volume flow rate of the infusion pump does not accurately reflect the flow rate in the drip chamber. When such movement occurs, existing apparatus have the disadvantageous feature of stopping the infusion pump and ceasing infusion.

Hence, those skilled in the art have recognized a need for an apparatus and a method to ensure continuous and accurate infusion even where uncontrollable environmental conditions cause the infusion system, specifically the drip chamber, to move. The invention fulfills these needs and other.

SUMMARY OF THE INVENTION

Briefly, and in general terms, the invention is directed to a method and apparatus for controlling infusion volume through an infusion pump. In one aspect, the invention comprises a method of controlling the fluid-flow rate of infusion fluid through an infusion pump that is receiving infusion fluid from a drip chamber. The method includes the step of measuring the flow rate of infusion fluid into the drip chamber and the step of monitoring the drip chamber for movement. If drip-chamber movement is not detected, the method further includes the step of setting the fluid-flow rate of the infusion pump to substantially match the fluid-flow rate of the drip chamber. If, however, drip-chamber movement is detected, the method then further includes the step of omitting the setting step and instead maintaining the fluid-flow rate of the infusion pump as set immediately prior to the detection of drip-chamber movement.

In another aspect, the invention comprises an apparatus for controlling the flow rate of infusion fluid through an infusion pump. The infusion pump receives infusion fluid from a drip chamber that has a fluid-flow rate; the fluid-flow rate of the infusion pump is set to substantially match the fluid-flow rate of the drip chamber. The apparatus includes a motion sensor that detects drip-chamber movement and generates a motion-detection signal that indicates the motion state of the drip-chamber. Also included is a controller that is coupled to receive the motion-detection signal from the motion sensor. If drip-chamber movement is detected, the controller maintains the fluid-flow rate of the infusion pump as set immediately prior to the detection of drip-chamber movement.

In yet another aspect, the invention comprises an apparatus for controlling the flow rate of infusion fluid through an infusion pump that receives infusion fluid from a drip chamber. The apparatus includes a flow sensor that detects drops of infusion fluid that enter the drip chamber and generates a drop-detection signal that indicates each drop detected. Also included is a setting controller coupled to receive the drop-detection signals from the flow sensor. The setting controller counts the detected drops and determines the fluid-flow rate of infusion fluid into the drip chamber. The setting controller then sets the fluid-flow rate of the infusion pump to substantially match the fluid-flow rate of the drip chamber. The apparatus further includes a motion sensor that detects drip-chamber movement and generates a motion-detection signal that indicates the motion state of the drip-chamber. A maintaining controller is coupled to receive the motion-detection signal from the motion sensor. The maintaining controller stores a signal that indicates a stationary drip chamber. The maintaining controller compares the motion-detection signal to the stored signal to determine if drip chamber movement has occurred. If drip-chamber movement has occurred the maintaining controller then maintains the fluid-flow rate of the infusion pump as set immediately prior to the detection of drip-chamber movement.

These and other aspects and advantages of the present invention will become apparent from the following more detailed description, when taken in conjunction with the accompanying drawings which illustrate, by way of example, the preferred embodiments of the invention.

DETAILED DESCRIPTION OF PREFERRED EMBODIMENTS

Figure 1:
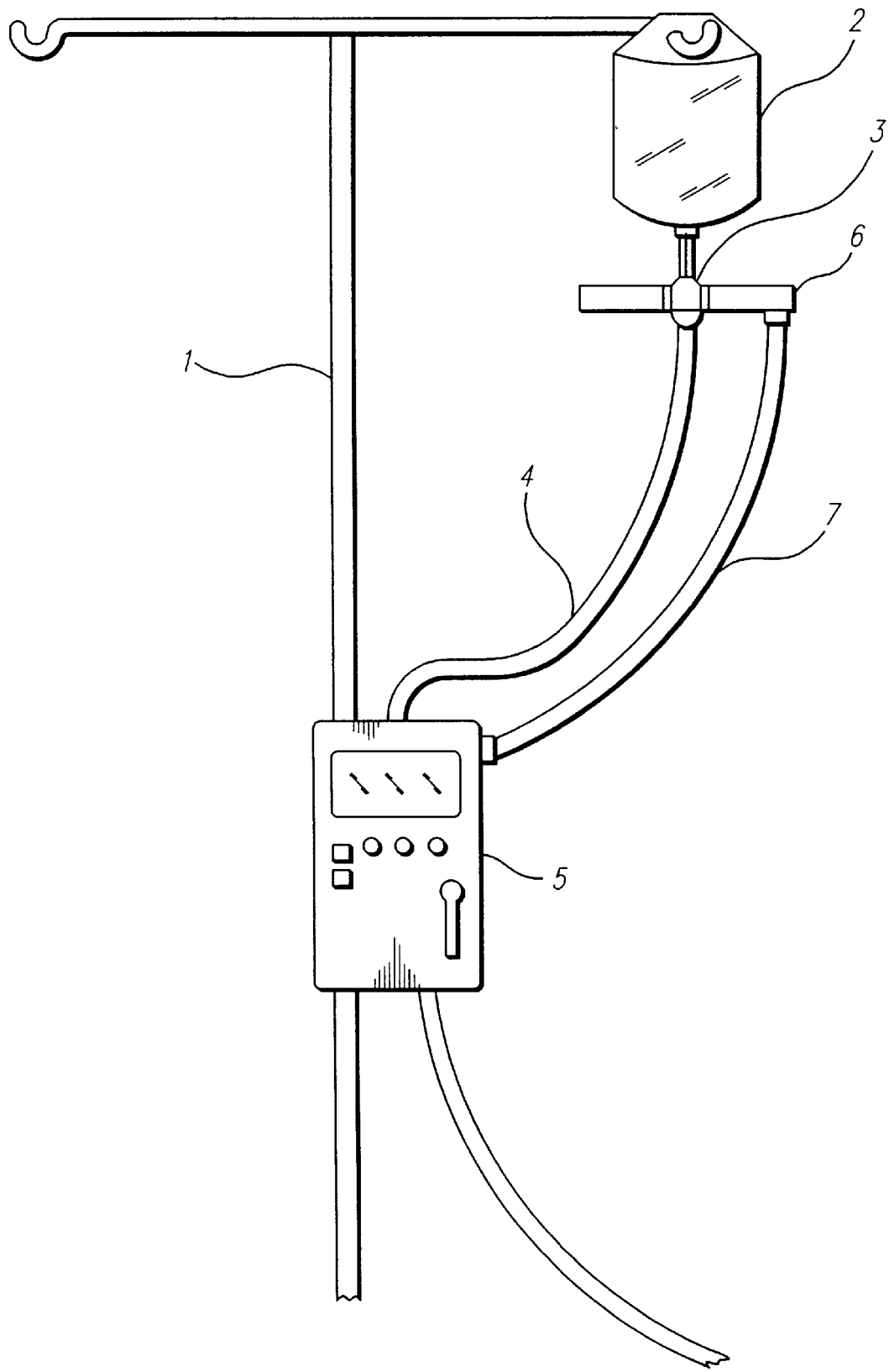
FIG. 1 is a side elevation view showing an outlined configuration of an infusion system having an infusion volume control apparatus according to a preferred embodiment of the invention.

Turning now to the drawings with more particularity, in FIG. 1 there is shown an infusion system that is equipped with an infusion liquid container 2. A drip chamber 3 communicates with, and receives fluid from the infusion liquid container 2. An infusion tube 4, in turn, communicates with the drip chamber 3 and receives fluid therefrom. The infusion tube 4 passes through an infusion pump 5 which controls the rate at which fluid flows through the infusion tube 4. The infusion liquid container 2 and infusion pump 5 are supported by an infusion stand 1. A drip monitoring device 6 is attached to the drip chamber 3. A controller (not shown) controls the operation of the infusion pump and is preferably incorporated into the infusion pump 5. The drip monitoring device 6 and controller interface through a cable 7.

Figure 2:
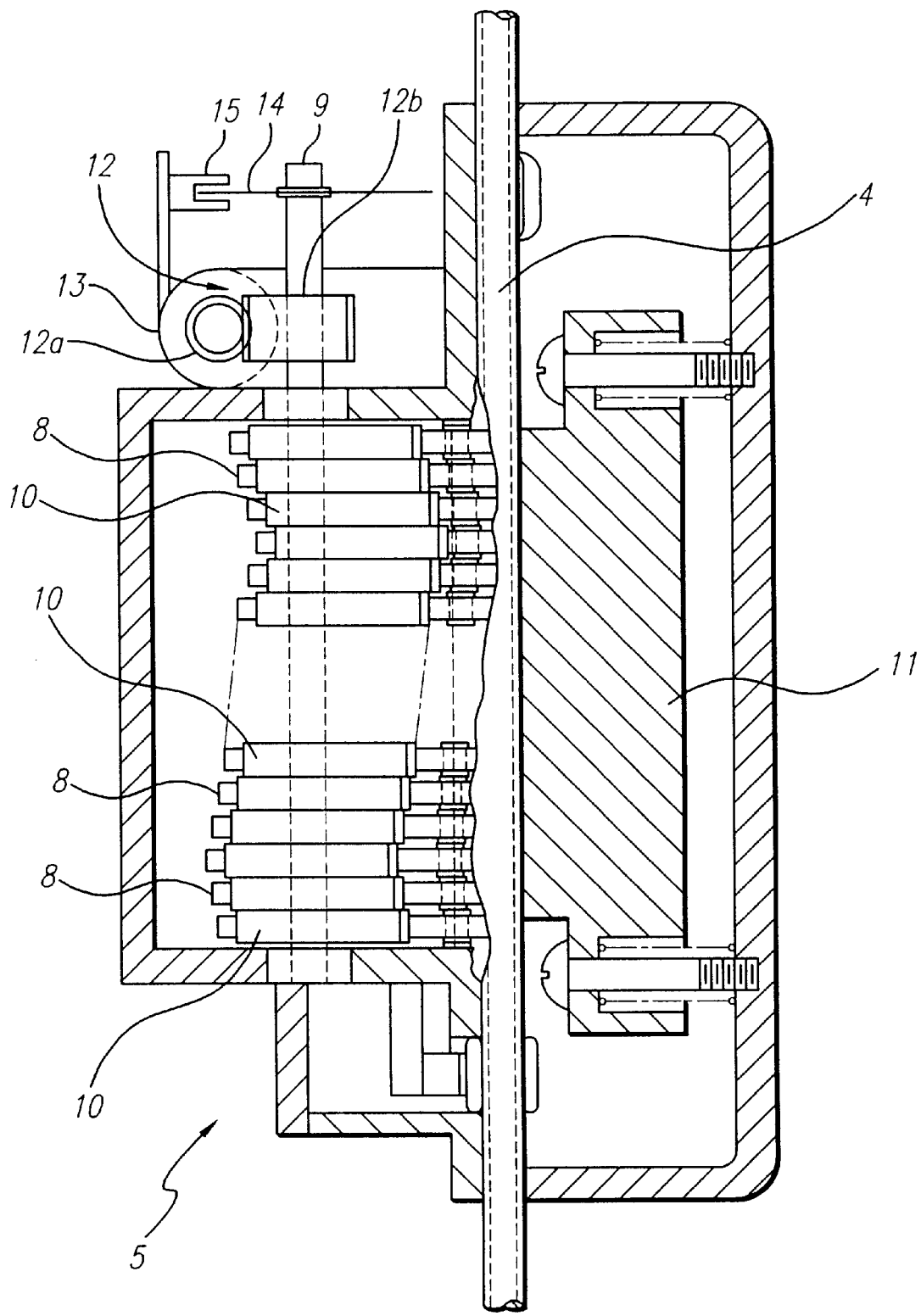
FIG. 2 is a longitudinal-sectional view of an infusion pump which is part of the infusion system of FIG. 1.

The infusion pump 5 as shown in FIG. 2 is provided with a plurality of horizontally movable finger members 8 disposed in a multi-layered fashion. A plurality of eccentric cams 10, one for each finger member 8, are pivotally stacked on a rotatable drive shaft 9. The eccentric cams 10 rotate together with the drive shaft 9. The finger members 8 are constructed so as to carry out peristaltic movements in line with the rotation of the drive shaft 9 and eccentric cams 10. This motion causes the finger members 8 to press against the infusion tube 4. Pressure plate 11 limits the movement of the infusion tube 4 and, together with the finger members 8, acts to compress the infusion tube 4 thereby transferring the infusion fluid in the tube 4 downward. The upper end of the drive shaft 9 is connected to a motor 13 through a transmission mechanism 12. The transmission mechanism includes a worm gear 12a; engaged with the worm gear 12a is a gear 12b. An encoder 14 is attached to the drive shaft 9 while a rotation position detector 15 is aligned with the encoder 14.

Figure 3:
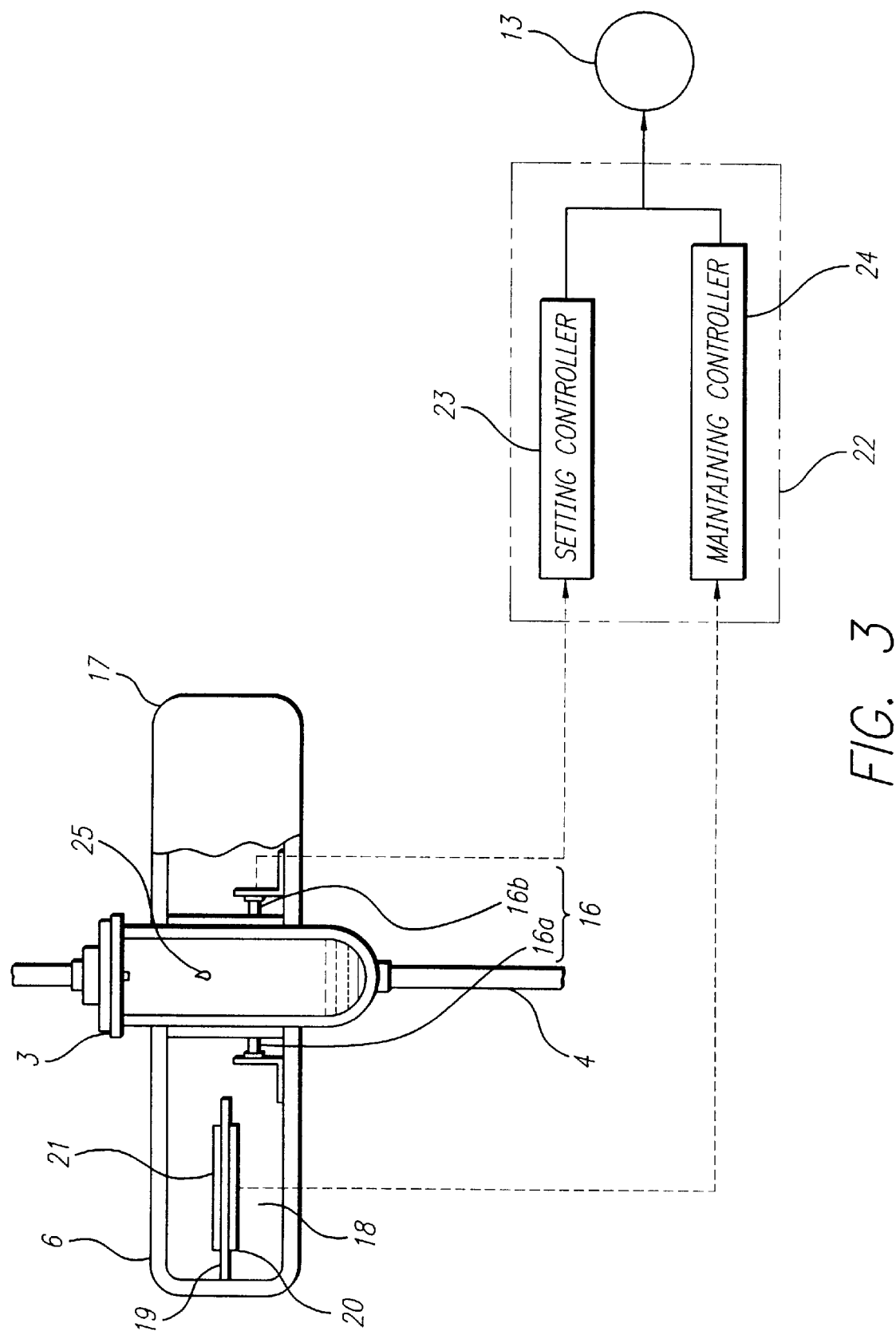
FIG. 3 is a longitudinal-sectional view of a drip monitoring device which is part of the infusion volume control apparatus of FIG. 1, also depicted is a block diagram of a controller which is also part of the infusion volume control apparatus of FIG. 1.

The drip monitoring device 6 as shown in FIG. 3 has a flow sensor 16 which detects fluid drops 25 entering the drip chamber 3. The flow sensor 16 is a photo coupler consisting of a light-emitting element 16a and light-receiving element 16b which are disposed in a casing 17. The casing 17 is attached to the drip chamber 3 so that the drip chamber 3 is positioned between the light-emitting element 16a and light-receiving element 16b. When a drop of fluid 25 passes through the drip chamber 3 it passes between the light-emitting element 16a and light-receiving element 16b. When this occurs the intensity of light received by the light-receiving element 16b is reduced and a drop is thereby detected. The flow sensor 16 generates an electrical signal based on the light intensity received by the light-receiving element 16b. Typically, a reduction in light intensity results in a reduction in the voltage of the electrical signal. The flow sensor 16 is electrically coupled to the controller 22 which is typically a microcomputer and is usually incorporated into the infusion pump.

A motion sensor 18 for detecting swaying or vibration of the drip chamber 3 is disposed in the drip monitoring device 6. Because the drip monitor device 6 is attached to the drip chamber 3, any movement of the drip chamber 3 results in a corresponding movement of the motion sensor 18. The motion sensor 18 includes a vibration detector 20. In an alternate configuration the motion sensor 18 also includes a vibration generator 21 and a metallic shim 19 positioned between the vibration detector 20 and the vibration generator 21. The vibration detector 20 and a vibration generator 21 are preferably piezoelectric ceramic elements. The motion sensor 18 is electrically coupled to the controller 22.

In operation, the voltage level of the electrical signal generated by the flow sensor 16 is monitored by a setting controller 23, contained in the controller 22. Based on the fluctuation in the voltage level of the electrical signal caused by fluid drops passing between the light emitting element 16a and the light receiving element 16b, the setting controller 23 counts the number of drops entering the drip chamber for a set period of time. The setting controller 23 then calculates the volume flow rate of fluid into the drip chamber 3 and, based on this calculation, sets the number of revolutions of the motor 13 which, in turn, sets the infusion volume flow rate of the infusion pump 5.

Movement of the drip chamber causes a corresponding movement or vibration of the vibration detector 20. The frequency of vibration of the vibration detector 20 due to drip-chamber movement is generally low, as for example 10 Hz. The movement of the vibration detector 20, in turn, produces an electrical signal whose voltage level fluctuates with the frequency of vibration of the vibration detector 20. In the alternate configuration of the motion sensor 18, the vibration generator 21 is used to verify the operation of the vibration detector 20. The vibration generator 21 is forced to vibrate at a known frequency, typically 60 Hz, through the application of an AC voltage signal. The vibration of the vibration generator 21 is transmitted to the vibration detector 20 through the shim 19. If operating properly, the vibration detector 20 vibrates at the same frequency of the vibration generator 21 and, again, produces a corresponding voltage.

A maintaining controller 24, also contained in the controller 22, monitors the voltage level received from the motion sensor 18 and compares it to the voltage level associated with a stationary drip chamber. The maintaining controller is programmed to distinguish voltages indicating drip-chamber movement, i.e., voltages associated with frequencies around 10 Hz, from voltages indicating a stationary drip chamber, i.e., the voltage associated with a frequency of around 0 Hz for a motion sensor 18 consisting only of a vibration detector 20 and the voltage associated with a frequency of around 60 Hz for a motion sensor 18 which includes the vibration generator 21 and the shim 19.

If a voltage indicating drip-chamber movement is received by the maintaining controller 24, the maintaining controller 24 overrides the setting controller 23 and the number of revolutions of the motor 13 remains as set immediately prior to the detection of drip-chamber movement. Otherwise the setting controller 23 sets the number of revolutions of the motor 13 so that the fluid-flow rate through the infusion pump 5 matches the fluid-flow rate through the drip chamber 3. While the setting controller 23 and the maintaining controller 24 are described as separate components of the controller 22, their functions may actually be performed by a single component, as for example a programmed microprocessor.

Figure 4:
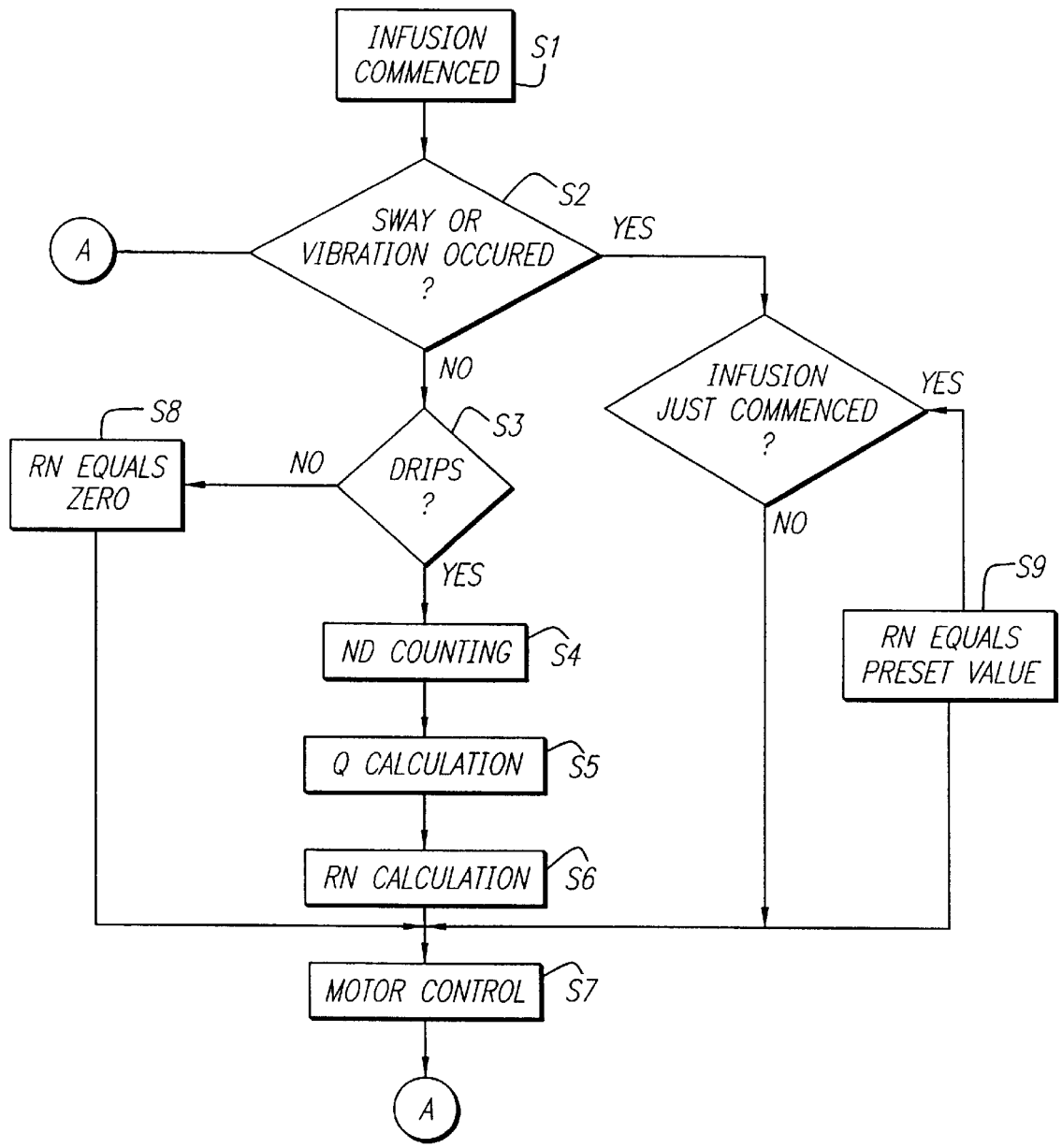
FIG. 4 is a flow chart depicting the operational steps of the controller of FIG. 3.

In summary, the controller performs a series of steps as shown in FIG. 4 that determines the volume flow rate of the infusion pump. In step S1, operation of the infusion pump is commenced. In step S2, the controller determines whether the signal it receives from the motion sensor indicates that drip-chamber movement has occurred. If drip-chamber movement has not occurred, in step S3 the controller determines, based on the signals received from the flow sensor, whether drops (D) are being detected by the flow sensor.

If drops are being detected, in step S4 the controller counts the number of drops (Nd) for a fixed period of time, e.g., 100 msec. In step S5, the controller calculates the volume (Q) of the infusion fluid that has entered the drip chamber in the fixed period of time based on the number of drops counted in step S4 and a known volume of one drop (Qo). The total volume is calculated using the expression Q=Nd×Qo. In step S6, the controller, having calculated the infusion volume in the drip chamber, calculates the number of revolutions (RN) of the motor necessary to set the infusion volume of the infusion pump to match that of the drip chamber. In step S7, the controller sends a control signal to the infusion-pump motor to set the number of revolutions of the motor to match that calculated in step S6. Thereafter, the process is returned to step S2.

In step S3, when no drops are detected for a fixed period of time, an infusion malfunction is issued. In step S8, the controller sets the number of revolutions of the motor in step S7 to zero, thereby causing the motor to a stop.

In step S2, when drip-chamber movement is detected and infusion has just commenced, the controller sets the number of revolutions of the motor in step S7 to a predetermined value as set in step S9. The predetermined value is typically programmed into the controller. When drip-chamber movement is sensed in step S2 and infusion has previously commenced the operation of the controller advances to step S7 and thereby bypasses a change in the motor revolutions (RN). Accordingly, the motor continues to run at the number of revolutions that had been obtained immediately beforehand. In this situation, where the flow sensor cannot detect all drops entering the drip chamber and the controller cannot accurately count the number of drops, the infusion volume of the infusion pump is maintained at the infusion rate obtained immediately prior to drip-chamber movement. As a result, it is possible to secure accurate and continuous infusion regardless of the environmental conditions under which the infusion system is operating.

While several particular forms of the invention have been illustrated and described, it will be apparent that various modifications can be made without departing from the spirit and scope of the invention. Accordingly, it is not intended that the invention be limited, except by the appended claims.

What is claimed is:

1. A method of controlling the fluid-flow rate of infusion fluid through an infusion pump receiving infusion fluid from a drip chamber, the method comprising the steps of:

measuring the flow rate of infusion fluid into the drip chamber;

monitoring the drip chamber for movement;

if drip-chamber movement is not detected, then setting the fluid-flow rate of the infusion pump to substantially match the fluid-flow rate of the drip chamber;

if drip-chamber movement is detected, then omitting the setting step and instead maintaining the fluid-flow rate of the infusion pump as set immediately prior to the detection of drip-chamber movement.

2. The method of claim 1 wherein the step of monitoring the drip chamber for movement comprises the steps of:

defining a signal that indicates a stationary drip chamber;

generating a signal that indicates the motion state of the drip chamber; and comparing the generated signal to the defined signal.

3. The method of claim 2 wherein the defined signal and the generated signal are voltage levels.

4. The method of claim 1 further comprising the step of setting the fluid-flow rate of the infusion pump to a predetermined rate if drip-chamber movement is detected at the commencement of infusion pump operation.

5. The method of claim 1 further comprising the step of setting the fluid-flow rate of the infusion pump to substantially zero if the flow rate of infusion fluid into the drip chamber is substantially zero.

6. An apparatus for controlling the flow rate of infusion fluid through an infusion pump, the infusion pump receiving infusion fluid from a drip chamber having a fluid-flow rate, the fluid-flow rate of the infusion pump being set to substantially match the fluid-flow rate of the drip chamber, the apparatus comprising:

a motion sensor that detects drip-chamber movement and generates a motion-detection signal indicating the motion state of the drip-chamber; and a controller coupled to receive the motion-detection signal from the motion sensor;

wherein, if drip-chamber movement is detected, the controller maintains the fluid-flow rate of the infusion pump as set immediately prior to the detection of drip-chamber movement.

7. The apparatus of claim 6 wherein the controller stores a signal that indicates a stationary drip chamber, and the controller compares the motion-detection signal to the stored signal to determine if drip-chamber movement has occurred.

8. The apparatus of claim 6 wherein the motion sensor comprises a piezoelectric element.

9. The apparatus of claim 6 wherein the motion sensor comprises:

a vibration detector that produces a voltage when it vibrates, the voltage being related to the frequency of vibration; and means for verifying proper operation of the vibration detector.

10. The apparatus of claim 9 wherein the verification means comprises:

means for inducing the vibration detector to vibrate at a known frequency; and means for measuring the voltage produced by the vibration detector and comparing it to the voltage that corresponds to the known frequency.

11. The apparatus of claim 10 wherein the inducing means comprises:

a vibration generator accepting an electronic signal that causes it to vibrate at the known frequency;

a metal shim; and wherein the vibration detector and the vibration generator are adjacent each other with the metal shim therebetween, and the metal shim is in contact with both the vibration detector and the vibration generator.

12. The apparatus of claim 11 wherein the electronic signal comprises an AC voltage signal and the predefined frequency is about 60 Hz.

13. The apparatus of claim 11 wherein the vibration detector and vibration generator comprise piezoelectric elements.

14. An apparatus for controlling the flow rate of infusion fluid through an infusion pump, the infusion pump receiving infusion fluid from a drip chamber, the apparatus comprising:

a flow sensor for detecting drops of infusion fluid that enter the drip chamber and generating a drop-detection signal that indicates each drop detected;

a setting controller coupled to receive the drop-detection signals from the flow sensor;

wherein the setting controller counts the detected drops, and determines the fluid-flow rate of infusion fluid into the drip chamber, and sets the fluid-flow rate of the infusion pump to substantially match the fluid-flow rate of the drip chamber;

a motion sensor that detects drip-chamber movement and generates a motion-detection signal that indicates the motion state of the drip-chamber;

a maintaining controller coupled to receive the motion-detection signal from the motion sensor; and wherein the maintaining controller stores a signal that indicates a stationary drip chamber and compares the motion-detection signal to the stored signal to determine if drip chamber movement has occurred, and, if drip-chamber movement has occurred, maintains the fluid-flow rate of the infusion pump as set immediately prior to the detection of drip-chamber movement.

15. The apparatus of claim 14 wherein the flow sensor and motion sensor are disposed in a casing that is coupled to the drip chamber.

16. The apparatus of claim 14 wherein the motion sensor comprises a piezoelectric element.

17. The apparatus of claim 14 wherein the setting controller and the maintaining controller are incorporated into the infusion pump.

18. An apparatus for controlling the flow rate of infusion fluid through an infusion pump, the infusion pump receiving infusion fluid from a drip chamber, the apparatus comprising:

a flow sensor for detecting drops of infusion fluid that enter the drip chamber and generating a drop-detection signal that indicates each drop detected;

a motion sensor that detects drip-chamber movement and generates a motion-detection signal that indicates the motion state of the drip-chamber;

a controller coupled to receive the drop-detection signals from the flow sensor and the motion-detection signal from the motion sensor;

wherein the controller counts the detected drops, and determines the fluid-flow rate of infusion fluid into the drip chamber, and sets the fluid-flow rate of the infusion pump to substantially match the fluid-flow rate of the drip chamber; and wherein the controller stores a signal that indicates a stationary drip chamber and compares the motion-detection signal to the stored signal to determine if drip chamber movement has occurred, and, if drip-chamber movement has occurred, maintains the fluid-flow rate of the infusion pump as set immediately prior to the detection of drip-chamber movement.

* * * * *